United States Patent [19]

Schmitt

[11] Patent Number: 5,741,332

[45] Date of Patent: Apr. 21, 1998

[54] THREE-DIMENSIONAL BRAIDED SOFT TISSUE PROSTHESIS

[75] Inventor: Peter J. Schmitt, Garnerville, N.Y.

[73] Assignee: Meadox Medicals, Inc., Oakland, N.J.

[21] Appl. No.: 545,060

[22] Filed: Oct. 19, 1995

Related U.S. Application Data

[63] Continuation of Ser. No. 376,898, Jan. 23, 1995, abandoned.

[51] Int. Cl.$^6$ .................................. A61F 2/04; A61F 2/06
[52] U.S. Cl. ................................................ 623/12; 623/1
[58] Field of Search ................................... 623/1, 11, 12, 623/13; 606/195, 194; 600/36

[56] References Cited

U.S. PATENT DOCUMENTS

| | | |
|---|---|---|
| 161,272 | 3/1875 | Van et al. . |
| 200,272 | 3/1878 | Baker . |
| 299,017 | 5/1884 | Schenck et al. . |
| 299,018 | 5/1884 | Schenck et al. . |
| 348,698 | 9/1886 | Sibley . |
| 427,929 | 5/1890 | Stowe . |
| 486,620 | 11/1892 | Stowe . |
| 532,902 | 1/1895 | Palmer . |
| 610,463 | 9/1898 | Stowe . |
| 697,391 | 4/1902 | Beck et al. . |
| 697,392 | 4/1902 | Beck et al. . |
| 899,092 | 9/1908 | Alvord . |
| 1,164,304 | 12/1915 | Nicewarner . |
| 2,025,039 | 12/1935 | Cannon . |
| 2,978,787 | 4/1961 | Liebig . |
| 3,000,076 | 9/1961 | Runton et al. . |
| 3,095,017 | 6/1963 | Bleiler et al. . |
| 3,105,492 | 10/1963 | Jacket . |
| 3,272,204 | 9/1966 | Artandi et al. . |
| 3,316,557 | 5/1967 | Liebig . |
| 3,317,924 | 5/1967 | LeVeen . |
| 4,025,684 | 5/1977 | Neidhardt . |
| 4,086,941 | 5/1978 | Thompson . |
| 4,193,137 | 3/1980 | Heck . |
| 4,312,261 | 1/1982 | Florentine . |
| 4,346,741 | 8/1982 | Banos et al. . |
| 4,416,028 | 11/1983 | Eriksson et al. . |
| 4,441,215 | 4/1984 | Kaster . |
| 4,670,286 | 6/1987 | Nyilas et al. . |
| 4,719,837 | 1/1988 | McConnell et al. . |
| 4,728,329 | 3/1988 | Mansat . |
| 4,743,250 | 5/1988 | Kitagawa et al. . |
| 4,834,747 | 5/1989 | Gogolewski . |
| 4,834,755 | 5/1989 | Silvestrini et al. . |
| 4,917,699 | 4/1990 | Chervitz . |
| 4,917,700 | 4/1990 | Aikins . |
| 4,923,470 | 5/1990 | Dumican . |
| 4,975,262 | 12/1990 | Suto et al. . |
| 5,084,065 | 1/1992 | Weldon et al. . |
| 5,091,246 | 2/1992 | Yasui et al. . |
| 5,116,360 | 5/1992 | Pinchuk et al. . |
| 5,178,630 | 1/1993 | Schmitt ............................ 623/1 |
| 5,273,080 | 12/1993 | Morohashi et al. . |
| 5,354,329 | 10/1994 | Whalen . |
| 5,357,839 | 10/1994 | Brookstein et al. . |
| 5,413,597 | 5/1995 | Krajicek . |

FOREIGN PATENT DOCUMENTS

| | | |
|---|---|---|
| 0 117 072 A1 | 8/1984 | European Pat. Off. . |
| 0 317 408 A1 | 5/1989 | European Pat. Off. . |
| 0 452 807 A3 | 9/1991 | European Pat. Off. . |
| 0 493 788 A1 | 7/1992 | European Pat. Off. . |
| 0 501 890 A1 | 9/1992 | European Pat. Off. . |
| 2548225 A1 | 1/1985 | France . |
| 2583072 A1 | 12/1986 | France . |
| WO 87/05796 | 10/1987 | WIPO . |
| WO 88/00813 | 2/1988 | WIPO . |
| WO 90/12550 | 11/1990 | WIPO . |
| WO 91/10766 | 7/1991 | WIPO . |

Primary Examiner—Debra S. Brittingham
Attorney, Agent, or Firm—Hoffmann & Baron, LLP

[57] ABSTRACT

The present invention provides a soft tissue prosthesis which is formed from a three-dimensional braided structure. The three-dimensional braided structure preferably may be made in the form of a solid three-dimensional braid, a three-dimensional braid having at least one interlocking yarn coupling contiguous layers or in the form of a plurality of two-dimensional braided layers adhesively laminated, separately sewn or otherwise connected together to form the three-dimensional braided prosthesis.

15 Claims, 3 Drawing Sheets

THREE-DIMENSIONAL BRAIDED SOFT TISSUE PROSTHESIS

This is a continuation of application Ser. No. 08/376,898 filed on Jan. 23, 1995, now abandoned.

BACKGROUND OF THE INVENTION

The present invention relates to a braided soft tissue prosthesis and, more particularly, to a soft tissue prosthesis formed from a three-dimensional braided structure.

Vascular grafts are commonly used as soft tissue prostheses to replace damaged or diseased veins and arteries. To maximize the effectiveness of any prostheses it is desirable that it have characteristics which closely resemble that of the natural body lumen.

One particular problem which is encountered is that of thrombosis. Thrombosis, or clotting, occurs when an individual's blood contacts a foreign body. As the blood begins to deposit platelets on the foreign body, a thrombus or blood clot forms. Historically, grafts having a relatively large diameter (greater than 10 mm) have generally proved successful over the long term because the build-up of thrombus that occurs on the interior surface of the graft is not sufficient to substantially obstruct the flow of blood. However, with respect to grafts having a diameter less than 10 mm, the build-up of thrombus on the interior surface of the graft can result in a complete obstruction of the graft in a relatively short period of time.

Presently, conventional tubular prostheses and, more specifically, vascular grafts formed by weaving or knitting synthetic fibers into a tubular structures, are susceptible to kinking or collapsing under varying circumstances, e.g., when the graft is bent during the contraction of surrounding muscle, or when external pressure is applied to the graft. One conventional solution to these problems has focused on the reinforcement of the walls of the vascular graft through the use of helically wrapped reinforcing fibers, reinforcing rings or bands placed externally around the tubular structure. The additional reinforcement of the tubular structure generally has the disadvantage of reducing the radial and/or longitudinal compliance of the graft due to the stiffness of the reinforcing member. A non-compliant graft may reduce the blood flow through the graft, thereby compromising the ability of the prosthesis to perform naturally. Additionally, the reinforcing member generally cannot be penetrated by cellular ingrowth from surrounding tissue and may cause the erosion of the surrounding tissue during contraction.

Another important characteristic associated with soft tissue prostheses is that of porosity. Preferably, the exterior surface of the prosthesis should include pores which are large enough to allow for the entry of connective tissue into the outer periphery of the graft. Conversely, the inner surface of the prosthesis must have pores small enough so that the blood or body fluid passing through the prosthesis will not leak into the prosthesis. Smaller pores on the inner surface of a vascular prosthesis also result in reduced platelet adhesion and a decreased amount of thrombus formation at the inner surface. Typically, a vascular prosthesis having a constant pore size throughout the structure requires pre-clotting in order to avoid leakage through the pores of the prosthesis; however, pre-clotting tends to increase the risk of contamination of the prosthesis as well as create a risk for clots to break off and form emboli.

Conventional tubular maypole (single layer) braided prosthesis have been tried in the past. However, due to their shortcomings, such prostheses have never been commercialized. One of the greatest disadvantages of a conventional tubular maypole braided prosthesis is the scissoring action which occurs under conditions of blood flow. More specifically, as blood is pumped through the graft, the pressure within the graft increases and decreases concurrently with the pumping of the heart, causing the yarns forming the braid to scissor correspondingly with the expansion and contraction of the graft. This scissoring action by yarns of the conventional maypole braided grafts tends to shear tissue which is attempting to grow into the vascular graft, thereby hindering the natural healing process and assimilation of the graft into natural tissue. Contrary to such conventional structures, the present invention concerns structures which due to their three-dimensional character are dynamically more stable and less prone to scissoring.

Yet another disadvantage of presently available woven or conventional tubular maypole braided prostheses is that sutures easily pull out making it difficult to attach the prosthesis to the existing body lumen and to prevent leakage at this junction. Also, since tubular prostheses are typically formed from a synthetic yarn in the form of a tube, the ends of the tube tend to easily ravel. This is true for single layered prostheses in general. Once the ends ravel or fray, suturing to the existing body lumen becomes extremely difficult. These difficulties explain the reason that these single layered braids have not been commercialized.

Accordingly, it would be advantageous to provide a new and improved soft tissue prosthesis that overcomes the previously-described disadvantages associated with presently available prostheses. More specifically, it would be particularly desirable to have a prosthesis which has the following characteristics: controlled porosity; ravel and fray resistance; a radially self-supporting structure to prevent kinking and collapsing of the prosthesis; and longitudinal compliance for ease of implantation and sizing.

SUMMARY OF THE INVENTION

The present invention addresses the problems associated with the prior art and provides a soft tissue prosthesis in the form of a three-dimensional braided structure preferably made from a synthetic material. The three-dimensional braided structure of the present invention is preferably a multi-layered braid, although a solid three-dimensional braided structure may also be formed. In the preferred embodiment, the braid includes a plurality of layers in which at least one strand of each layer extends into an adjacent or contiguous layer to interlock the adjacent layers; however, a graft may be formed in which the layers are interlocked by means other than by part of the braid itself. For example, the layers may be adhesively laminated, separately sewn together or otherwise connected to prevent separation. Preferably, the multi-layered braid of the present invention includes from two to about ten layers. The number of layers will depend on a number of factors such as the particular application involved, denier of yarns used and the strength of the yarn. The interlocking of the layers in the preferred embodiment helps to prevent separation or movement of the layers in relation to each other. Additionally, to enhance resistance to ravelling or fraying, at least one of the layers or yarns included in the three-dimensional braided structure may be formed from a fusible material, such as a thermoplastic material, which may be subsequently heated to integrally bond or fuse the layer or contiguous yarns into the braided structure.

The braids of the present invention may be used in a wide variety of applications for replacement of or in support of body lumens. For example, vascular grafts are among the most notable applications, but other lumens such as esophagical, intestinal, urethra, bile ducts and the like are contemplated. The term "soft tissue" prosthesis is intended to cover all such applications.

Among the vascular prosthesis areas which are specifically contemplated include, A-V access shunt grafts used for dialysis, small diameter (3–10 mm) peripheral grafts, tapered grafts, aortic arch grafts, dilatible pediatric grafts and vein grafts.

The three-dimensional braid of the present invention is preferably formed from synthetic materials, which are preferably thermoplastics. The thermoplastic may be chosen from a variety of usable thermoplastics which include, but are not limited to polyesters, polypropylenes, polyethylenes, polyurethanes and polytetrafluoroethylenes. The thermoplastic yarns may have a denier from about 20 to about 1000, and preferably from about 40 to about 300, whereby the smaller the denier the finer the yarn. Alternatively, the synthetic material may be in the form of rovings, tapes or other stranded materials. If yarns are used they may be multifilament, monofilament or spun type. Multifilaments are preferred. In applications where enhanced crush resistance is desired, the use of monofilaments may be effective in achieving this end. The yarns can be in the form of any conventional configuration, such as flat (untwisted), twisted, textured or pre-shrunk.

The prostheses of the present invention may be formed from a mixture of different yarns or the layers themselves may be formed from a single type of yarn. This determination will largely be a matter of choice as to the intended application and desired properties of the prosthesis. It is also contemplated that bioabsorbable materials, such as poly (glycolic acid), poly(lactic acid), polydioxanoes, polyoxalates, poly($\alpha$-esters), polycarbonates, polyanhydrides, poly acetals, polycaprolactones, poly (orthoesters), polyamino acids, polyurethanes, polyiminocarbonates, polyamindes, poly(alkyl cyanoacrylates), sebacic acid, polyethylene glycol, polyphosphazene, bis(p-carboxyphenoxy)propane, bis(p-carboxyphenoxy)methane and copolymers and mixtures thereof may be used as yarns to form a part of the three-dimensional braid. Yarns made from these materials are intended to be broken down and absorbed into the body, thereby leaving a void or pore behind in the prosthesis. Therefore, in an embodiment using bioabsorbable yarns, the porosity of the prosthesis can be varied and controlled in accordance with a particular absorption rate of the bioabsorbable material.

The type of yarn, the number of layers, the heat-set conditions and the angle at which the braid is formed determines the longitudinal flexibility and radial compliance of the vascular graft of the present invention. It should be noted that in the preferred embodiment, each layer of the multi-layered braid may be formed from a different synthetic yarn to accomplish different structural and functional characteristics required for the intraluminal and extraliminal surfaces of the prosthesis.

Generally, prostheses are designed to balance the longitudinal stretch, the kink resistance and the crush resistance of the structure for the particular application of the prosthesis. The longitudinal stretch of the prosthesis may be from about 5–50% of the unstressed length of the prosthesis, and preferably is about 10–25%. The longitudinal stretch of the prosthesis is directly related to the kink resistance or flexibility of the prosthesis, i.e., the greater the longitudinal stretch, the more kink resistant. Kink resistance can be defined as a ratio of the bending radius to the radius of the prosthesis. Typically, the kink resistance is not more than a 10:1 ratio, and preferably is less than about 5:1. The degree of crush resistance needed in the prosthesis depends upon the application. In some circumstances it is important that the crush resistance be high, while in other applications the crush resistance may be a minimal factor.

In an alternative embodiment, axial yarns may be added to the braided structure to control the amount of longitudinal or axial stretch. The axial yarns may be included in any single layer or in each layer of the braid and may be formed from any number of types of yarn (monofilament, multifilament, fine denier or heavy denier) depending upon the application of the prosthesis being formed. The axial yarns also help to reduce scissoring of the yarns under conditions of pressure increases and reductions within the lumen of the prosthesis by controlling the amount of longitudinal stretch of the prosthesis. The axial yarn reduces the scissoring effect of the yarns by limiting the angle of the braided yarns from dropping below a chosen braid angle measured in relation to the longitudinal axis of the braided structure, for example, 54.5° which is the neutral angle for pressure vessels.

The soft tissue prosthesis of the present invention provides a method for controlling the permeability or porosity at each layer of the prosthesis to correspond to the requisite characteristics. In the preferred embodiment, the prosthesis formed in accordance with the present invention includes relatively small pores at the intraluminal surface and relatively large pores on the outer surface. The intraluminal surface is substantially smooth and preferably has a small porosity to prevent blood leakage as well as to reduce excessive thrombus from forming on the intraluminal surface of the prosthesis. The outer surface preferably has a high porosity to promote ingrowth of connective tissue therethrough. The composite porosity from the intraluminal surface measured using a Wesolowski water permeability test should not exceed 100 ml/minute/cm$^2$. If a more porous prosthesis is formed, it may be treated, coated, or impregnated with materials such as collagen to make them leak resistant.

Accordingly, a prosthesis may be formed in accordance with the present invention wherein the average pore diameter of the outer surface is larger than the pores formed on the intraluminal surface and the pore size changes progressively within the three-dimensional braided structure. The prostheses of the present invention may include a gradation or differential of properties between their intraluminal and outer surfaces. In a preferred embodiment, the pores of the three-dimensional braided structure form a tortuous path from the intraluminal surface to the outer surface of the prosthesis.

The three-dimensional braided structure of the present invention also has the advantage of being radially self-sustaining. More specifically, the three-dimensional tubular braid is more kink resistant and crush resistant than conventional woven, knitted or conventional tubular maypole braided (single layer) prostheses of the past, most of which required external support and crimping. The prostheses of the present invention allow for a straight inner wall to be maintained, whereas a crimped prosthesis creates problems in body fluid flow, i.e., undesirable turbulence, and in deposition of material in the peaks and valleys of the crimp. The radially self-sustaining feature of the inventive structures makes them more desirable for use in prostheses having small diameters, and preferably, having a diameter of less than 10 mm and in applications in the body where radial self-sustenance is of concern.

As previously mentioned, the prostheses of the present invention are formed from a three-dimensional braided structure. In this regard, it is possible to form the prosthesis on a shaped article or mandrel. For example, it may be advantageous to form a prosthesis that is tapered in order to more closely match the two ends of the body lumen which it is replacing. Also, in a three-dimensional braiding process, it is possible to form bifurcations, trifurcations or multiple tubular structures. These structures may also be formed by joining a plurality of three-dimensional braided tubes by sewing or other appropriate means for attaching the braided structures. Additionally, a three-dimensional braid may be formed on a shaped mandrel or preform to correspond to the curvature of the body lumen being replaced. Preshaping a vascular prosthesis may be advantageous when replacing blood vessels such as the aortic arch, which have exaggerated or sharp bends.

A suitable method of making prostheses in accordance with the present invention includes choosing a mandrel with an outside diameter corresponding to an inside diameter of a natural body lumen which is to be replaced and braiding a three-dimensional braided structure on the mandrel. In the multi-layered prosthesis, the layers can be braided one at a time, i.e., forming a completed layer and braiding over the completed layer to form the next layer, or several layers may be formed simultaneously. The three-dimensional structure is preferably heat-conditioned for a sufficient time and temperature to heat-set the material, preferably thermoplastic yarn, used to form the prosthesis. The braided structure may include a fusible component which when subsequently heated melts to enhance the ravel and fray resistance of the braid. In a preferred embodiment, the three-dimensional multi-layered braid includes a first or inner layer formed from a yarn having a fine denier, a second layer including a stiffening component, a third layer formed from a fusible component, and a fourth or outer layer formed to have a textured surface, i.e. a velour. In this embodiment, the textured outer surface may include relatively large pores to allow ingrowth of connective tissue into the graft and the intraluminal or first layer may include small pores to prevent fluid from leaking out of the prosthesis. The inner layer is also braided to provide a smooth, straight inner surface which enhances fluid flow and resists deposition of materials which may cause stenosis or occlusion.

A preferred form of the three-dimensional braided structure, as well as other embodiments, features and advantages of this invention will be apparent from the following detailed description of illustrative embodiments thereof, which is to be read in connection with the accompanying drawings.

DETAILED DESCRIPTION OF THE INVENTION

The present invention is directed to a soft tissue prosthesis and, more specifically, to a three-dimensional braided structure. The prosthesis formed in accordance with the present invention overcomes many of the disadvantages of presently used conventional soft tissue prosthesis including controlling porosity throughout the tubular structure, forming a prosthesis which is longitudinally elastic as well as being ravel and fray resistant and able to hold sutures. As previously described, it is advantageous to design a prosthesis that has characteristics closely resembling the properties of a natural body lumen.

For purposes of this application, the term soft tissue prosthesis is defined as any artificial substitute for a natural body lumen such as a vein, artery, esophagus or a bile duct. Although some of the discussion in the detailed description is directed to use as a vascular graft, it is envisioned that the three-dimensional tubular braided structure of the present invention can be useful as a prosthesis for any soft tissue body lumen. Naturally, the tubular braided structure would be designed to meet the specific requirements of the body lumen it is replacing.

A multi-layered braided structure is defined as a structure formed by braiding wherein the structure has a plurality of distinct and discreet layers. These layers may be bound by interlocking yarns or by adhesive laminates, sewing, or the like.

A solid three-dimensional braided structure is defined as a structure braided with no less than three braiding yarns which are continuously intertwined through the thickness of the braided structure. Solid braids are homogeneous in that all yarns are present throughout the thickness of the braid. These braids can be thought of as a series of plys which are integrally bound through the braid.

An interlocking three-dimensional braid is defined as a braided structure having at least two layers, whereby a yarn is interbraided from a first layer into a contiguous second layer to interlock the layers of a multi-layered braid.

A three-dimensional braided structure is defined as a braided structure formed in accordance with the definition of a multi-layered braid, a solid three-dimensional braid or an interlocking three-dimensional braid.

Figure 1:
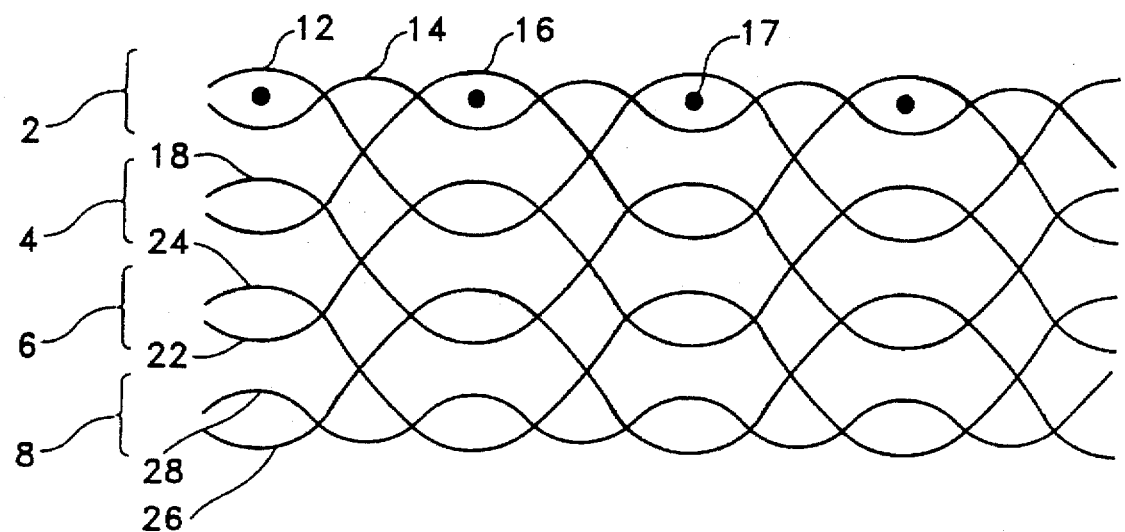
FIG. 1 is a cross-sectional view of a portion of a multi-layered interlocked three-dimensional braided prosthesis formed in accordance with the preferred embodiment of the present invention.

In accordance with the present invention, the three-dimensional braid is preferably a multi-layered braid having an interlocking yarn between the layers of the braid as illustrated in FIG. 1. The interlocking yarn extends from one layer into another contiguous layer in order to interlock the layers together.

Referring to FIG. 1, the soft tissue prosthesis of the preferred embodiment of the present invention comprises four layers, 2, 4, 6 and 8, with each layer having at least one interlocking yarn from a contiguous layer. The interlocking yarns are braided into the structure so that the yarn forms part of a first layer, as well as being part of the contiguous layer by forming the interlock. Within each layer, a segment of the braid is formed by an interlocking yarn from a contiguous layer, the layers being interbraided together. The interlocking yarns couple the multiple layers together to form a three-dimensional braid.

In FIG. 1, the first layer 2 forms the outer layer of the interlocking three-dimensional braided structure. The outer layer is formed from a yarn 14 which is exclusively braided into the first layer along with a yarn 12 which is interbraided into the second layer which is contiguous with the first layer and a yarn 16 which is interbraided from the second layer up into the first layer. The second layer 4 is formed from segments of four yarns 12, 16, 18 and 22 which are interbraided.

The next contiguous layer 6 is formed from segments of four yarns 18, 22, 24 and 26 interbraided to form an inner layer in the multi-layered structure. Layer 8 is formed in similar fashion, having three yarns 24, 26 and 28 which are interbraided.

A braiding machine capable of forming the interlocked three-dimensional braid used to form the preferred embodiment of the present invention is described in International Patent Publication No. WO 91/10766, incorporated herein by reference, which describes a braiding machine capable of forming a multi-layered braid having a yarn from one layer interlocking with a contiguous layer. This apparatus will be described later in greater detail.

Figure 2:
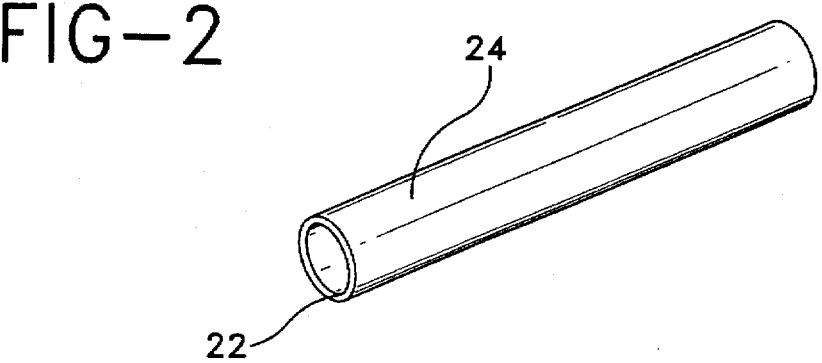
FIG. 2 is a perspective view of a tubular three-dimensional braided structure formed in accordance with the present invention.

FIG. 2 is a perspective view of a tubular three-dimensional braided prosthesis formed in accordance with the present invention. The prosthesis is in the form of a tube having an intraluminal surface 22 and an extraluminal or outer surface 24. The three-dimensional braid is formed to provide a balance of properties and give the longitudinal stretch, kink resistance or flexibility and crush resistance required for the particular application. The longitudinal stretch of the prosthesis may be from about 5–50% of the unstressed length of the prosthesis, and preferably is about 10–25%. The longitudinal stretch of the prosthesis has been found to be directly related to the kink resistance or flexibility of the prosthesis, i.e., the greater the longitudinal stretch, the more kink resistant the prosthesis. Kink resistance can be defined as a ratio of the bending radius to the radius of the prosthesis. Typically, the kink resistance is not more than about a 10:1 ratio, and preferably is less than about 5:1. The crush resistance of the prosthesis depends upon the application. In some circumstances it is important that the crush resistance be high, while in other applications the crush resistance may be of minimal concern.

Figure 3:
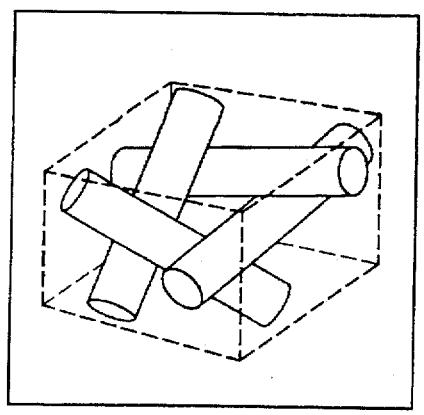
FIG. 3 is a schematic illustration of a solid three-dimensional braid unit cell formed in accordance with one embodiment of the present invention.

FIG. 3 illustrates a solid three-dimensional braid cell unit formed in accordance with an alternative embodiment of the present invention. The solid three-dimensional braid achieves a seamless, multi-layered tube by continuous intertwining of fibers. The braid cell unit illustrated in FIG. 3 is the smallest unit showing the braid pattern.

Figure 4:
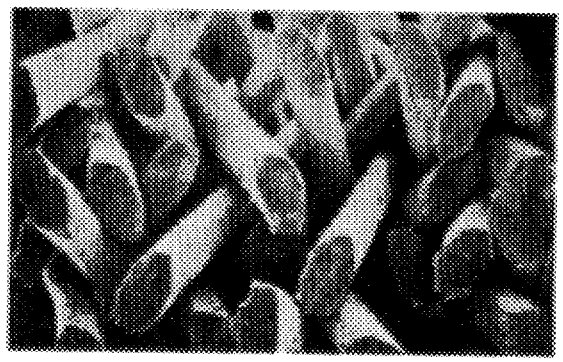
FIG. 4 is a photograph of an enlarged cross-section of a solid three-dimensional braided structure formed in accordance with one embodiment of the present invention.
Figure 5:
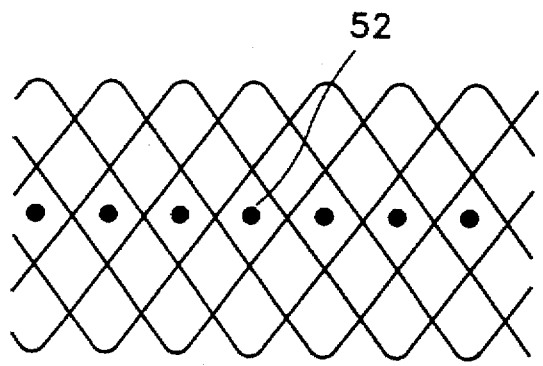
FIG. 5 is a cross-sectional view of a portion of a solid three-dimensional braided structure formed in accordance with one embodiment of the present invention.

FIG. 4 is an enlarged cross-sectional view of a solid three-dimensional braided structure formed by continuous intertwining of the fibers. In a solid three-dimensional braid, every yarn is present in each layer. Typically, three-dimensional braiding machines used to form this type of solid braid include an array of fiber bobbins held in ring or track configurations. Circumferential motion of the array of bobbins to form the braid is accomplished by shifting slotted rings containing the fiber holders. Fibers are directed through the thickness of the braid by shifting the holders between the rings. Reversal of the direction of ring and hold motions during the shift cycle interlocks the fibers as illustrated in the cross-sectional view shown in FIG. 5. Since every fiber undergoes a similar motion, all fibers become entwined in the balanced array as illustrated in FIGS. 4 and 5.

Figure 6:
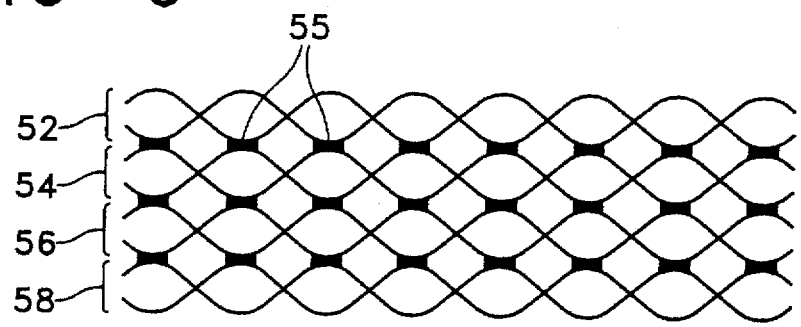
FIG. 6 is a cross-sectional view of a portion of a vascular graft formed in accordance with an alternative embodiment of the present invention.

In yet another embodiment of the present invention, a three-dimensional multi-layered braid may be formed from a plurality of individually and separately formed tubular braided layers which are adhesively laminated or sewn together in order to form a soft tissue prosthesis. The tubular layers must be concentric with respect to their mutual longitudinal axis. FIG. 6 illustrates a cross-sectional view of a portion of a prosthesis formed from a plurality of braided layers adhesively laminated together. The graft as shown in FIG. 6 includes four layers 52, 54, 56 and 58 which are coupled together by an adhesive laminate 55 at points of contact between contiguous layers. Each layer may be formed from a type of yarn having characteristics most desirable to its positioning within the prosthesis. For example, when designing a vascular graft, the inner layer which forms the intraluminal surface is preferably braided to have a smooth surface and a low porosity to prevent leakage of blood and excessive thrombus formation. Conversely, the outer surface is preferably braided to have a textured surface to enhance the ingrowth of connective tissue into the vascular graft.

The textured outer layer of this embodiment may also be formed by warp-knitting to create the velour surface. A velour surface is created by a knitting technique described in U.S. Pat. No. 4,193,137, entitled, "Warp-Knitted Double-Velour Prosthesis," the disclosure of which is incorporated herein by reference. An outer layer or tube may be knitted having a thread which passes back and forth through a wall or trellis of the fabric. These loops constitute the velour or pile. The loops on both faces thereof is termed a double-velour fabric. The velour fabric or tube made of the fabric may be placed around a multi-layered braided tubular prosthesis to form the outer layer of the prosthesis. The velour fabric or tube may be adhesively laminated, separately sewn, or otherwise connected to the multi-layered braid of the present invention. Alternatively, a velour-textured yarn may be used in place of another yarn in the braid.

The preferred embodiment of the interlocked three-dimensional multi-layered braid of the present invention includes between two and ten layers. Since the soft tissue prosthesis of the present invention is a multi-layered structure, a natural feature of such a structure is that it is ravel and fray resistant. Also, a multi-layered braided structure having interlocking yarns will hold a suture better than previously woven or knitted structures used for vascular grafts. The multi-layered braid of the present invention may also include at least one layer including a fusible material. The fusible material may be added to further prevent ravelling or fraying which may occur at the ends of the braid. In such an embodiment, the layer or portion of the layer which is formed from the fusible material, is heated to melt the fusible layer onto the surrounding yarns thereby further enhancing the ravel and fray resistance of the braided structure and providing a more suitable structure for suturing to a natural body lumen.

A soft tissue prosthesis formed in accordance with the present invention may be formed from braiding elements including yarns, rovings, tapes or other stranded material. Some of the yarns may be bioabsorbable with other yarns being merely biocompatible. By utilizing non-woven tapes, such as spunbonded fabric slit into, for example, 1/16" widths, a microporous structure can be formed. The spunbonded tapes are also an excellent medium for suturing. In this regard, the spunbonded tape is readily pierced by a suture needle yet possesses high tear strength and positive anchoring. Since these tapes are very thin and narrow, layers of different yarns may be incorporated into the multi-layered braid to provide additional mechanical strength to the prosthesis.

As mentioned above, the three-dimensional braided structure formed in accordance with the present invention may include one or more yarns formed from bioabsorbable materials. Suitable bioabsorbable materials include but are not limited to poly(glycolic acid), poly(lactic acid), polydioxanoes, polyoxalates, poly($\alpha$-esters), polycarbonates, polyanhydrides, polyacetals, polycaprolactones, poly(orthoesters), polyamino acids, polyurethanes, polyiminocarbonates, polyamindes, poly (alkyl cyanoacrylates), sebacic acid, polyethylene glycol, polyphosphazene, bis(p-carboxyphenoxy)propane, bis(p-carboxyphenoxy)methane and copolymers and mixtures thereof, provided that these materials can be formed into a fiber suitable for use with the braiding apparatus being used. A bioabsorbable yarn may be used in either a single layer, in several different layers, or as several yarns within a solid three-dimensional structure to form a prosthesis having an initial porosity different from the porosity once the bioabsorbable material has been absorbed into the body. Once absorbed, a void or pore remains in its place. This may be useful in designing a prosthesis having initially small pores to prevent leaking without the use of a sealant or pre-clotting and yet having a greater porosity to enhance ingrowth of connective tissue some time after implantation.

Of particular usefulness in forming the three-dimensional prosthesis are the polyester materials sold under the Dacron brand name. In the preferred embodiment of the present invention, synthetic yarns are used to form the braided prosthesis. The yarns may be flat, twisted, textured or pre-shrunk. Preferably, the yarns are thermoplastic yarns. Thermoplastic yarns suitable for use in forming the vascular graft include, but are not limited to polyesters, polypropylenes, polyethylenes, polyurethanes and polytetrafluoroethylenes. The yarns may be of the multifilament, monofilament or spun type. Multifilaments are preferred, however, where enhanced crush resistance is desired, the use of monofilaments may be effective in achieving this end.

Additionally, the yarn type and yarn denier for each layer are specifically chosen to meet the design requirements (porosity, flexibility and compliance) of the prosthesis, e.g. vascular graft being formed. Yarn denier denotes the linear density of the yarn (number of grams mass divided by 9,000 meters of length). Thus, a yarn having a small denier, e.g. 20, would correspond with a very fine yarn whereas a yarn having a large denier, e.g. 1000, would correspond to a heavy yarn. The yarns used to form the braid of the present invention may have a denier from about 20 to about 1000, and preferably from about 40 to about 300.

The type of yarn chosen and the denier of the yarn are important in order to form a prosthesis and, more specifically, a vascular graft having proper pore size. Porosity is important when designing a vascular graft because the intraluminal surface must have pores small enough to prevent the graft from leaking blood while the outer surface must have pores large enough to permit ingrowth of connective tissue and promote healing. Since a preferred embodiment of the present invention is a vascular graft having discrete layers, the designer of the graft can create a structure having different properties at each layer of the multi-layered braid. For example, the first or inner layer of the multi-layered vascular graft may be formed from a yarn having a fine denier and braided at a braid angle such that the intraluminal surface will be smooth and have a low porosity. The low porosity will prevent blood from leaking out of the vascular graft and the smooth intraluminal surface reduces excessive formation of thrombus. Conversely, the outermost layer of the vascular graft may be formed from a yarn having a larger denier and having a braid angle such that the surface is textured and has large pores. The high porosity of the outer surface permits connective tissue ingrowth into the vascular graft to promote healing. In the preferred embodiment, the composite porosity from the intraluminal surface to the outer surface measured using a Wesolowski water permeability test should not exceed 100 ml/minute/ $cm^2$. If a more porous prosthesis is formed, it may be treated, coated or impregnated with materials such as collagen to make it leak resistant.

The layers between the outer and inner layers of the vascular graft may be formed so that the pore size changes progressively from layer to layer within the multi-layered braided structure. The pores of the multi-layered braided structure as well as the solid three-dimensional braided structure preferably form a tortuous path from the intraluminal surface to the outer surface of the vascular graft of the present invention. Also, since the intraluminal surface of the graft can be made smooth and braided to have small pores to prevent leakage, the vascular graft of the present invention can be made so that it does not require a sealant, such as collagen, or to be pre-clotted prior to implantation. Thus, the vascular graft of the present invention may be manufactured ready-to-use unlike many woven or knitted conventional vascular grafts.

Another advantage of the three-dimensional braided structure for use as a soft tissue prosthesis or vascular graft is that the structure can be formed to be radially self-supporting. The three-dimensional braided structure can also be formed to provide the desired degree of longitudinal flexibility and stretch by varying the braid angle at which the braid elements or components are braided. The flexibility and stretch of the graft is also determined by the type of yarn and the denier of the yarn selected to form the braided structure. Thus, the three-dimensional braid of the present invention provides a vascular graft having characteristics which closely resemble that of a natural blood vessel. Also, three-dimensional multi-layered and solid braided vascular grafts having small diameters (i.e., less than 10 mm) may be formed having enhanced crush and kink resistance. Presently, conventional grafts made without external support or without crimping and having diameters less than 10 mm have not proven effective for use as a vascular graft since the graft tends to kink or crush, thereby restricting blood flow through the graft. Additionally, the prosthesis can be formed having a smooth, straight inner wall whereas if crimping is required, the inner wall forms peaks and valleys which creates problems in body fluid flow and deposition of materials in the peaks and valleys of the crimp.

The three-dimensional braided soft tissue prosthesis of the present invention may also be formed on a shaped mandrel in order to form a braid more closely resembling the length of soft body tissue being replaced. More specifically, the three-dimensional braid may be formed on a tapered mandrel or on a bent or curved mandrel to form a prosthesis. For example, if it is desired to replace the aortic arch, a vascular graft having an almost 90° bend will be required. It is possible to form a three-dimensional braided structure on a shaped mandrel which resembles the curvature of the aortic arch. The three-dimensional braid formed on the shaped mandrel provides a self-sustaining structure having an open lumen throughout the bend. Additionally, in a multi-dimensional braided structure, it is possible to form bifurcations, trifurcations or multiple tubular structures. This may be accomplished in a continuous process as the braided prosthesis is being formed, or by joining at least two three-dimensional braided tubes previously formed by sewing or other appropriate means for connecting the braided structures together to form a desired formation. Thus, a three-dimensional braided structure is more versatile in design than conventional woven, tubular maypole braided or knitted vascular grafts.

In an alternative embodiment, axial yarns may be added to the braided structure to control the amount of longitudinal or axial stretch and thereby control the scissoring action of the yarns. The axial yarns also control or limit the longitudinal stretch of the prosthesis so that the surgeon does not hyper-extend the prosthesis beyond its intended range during the implantation procedure. As illustrated in FIG. 1, the axial yarns 17 are longitudinally inserted within the braided structure during the braiding process to form a triaxial structure. A triaxial structure has three yarn axes as opposed to a simple braided structure which is biaxial and has two yarn axes.

Typically, the braided structure is formed having a braid angle from about 54.5° to about 90° with respect to the longitudinal axis of the braided structure, preferably about 54.5° to about 75° and, most preferably, from about 54.5° to about 90°. The yarns of the braid tend to seek equilibrium at a braid angle of about 54.5°, which is the neutral angle for tubular vessels under pressure. Thus, when the braid angle is larger than the neutral angle, when pressure is exerted from within, for example due to fluid flow, the yarns will tend to scissor and to decrease the braid angle thereby elongating or stretching the braided structure in order to reach the neutral angle. Axial yarns 17 are added in some cases to limit the braided structure from stretching beyond a desired amount, and thereby significantly reducing the potential for scissoring action of the yarns. This scissoring or shearing action is detrimental to the healing process. The scissoring action of the strands tends to prevent the tissue and blood vessels from filtrating the pores of the structure.

Figure 7:
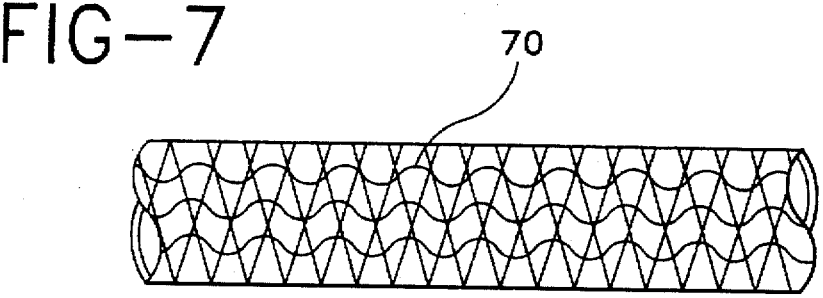
FIG. 7 is a side elevational view of a compressed braided structure having axial yarns therein.

Axial yarns used to limit the amount of longitudinal stretch in a braided prothesis may be formed from polyester, Teflon, polypropylene yarns or any other suitable material. Upon completion of the braiding process, the braided structure is preferably scoured to remove contaminants and subsequently heat-set. The heat-setting is preferably accomplished by compressing the braided structure onto a mandrel. The mandrel would be of greater diameter than the diameter of the braided structure. As illustrated in FIG. 7, compressing the braid onto the mandrel causes the diameter causes the diameter to increase, decreasing the length of the structure and causing the axial yarns 70 to slacken. Additionally, the angle of the braid becomes greater upon compression of the structure. The heat-setting process is dependent upon the types of yarns used to form the braid.

Figure 8:
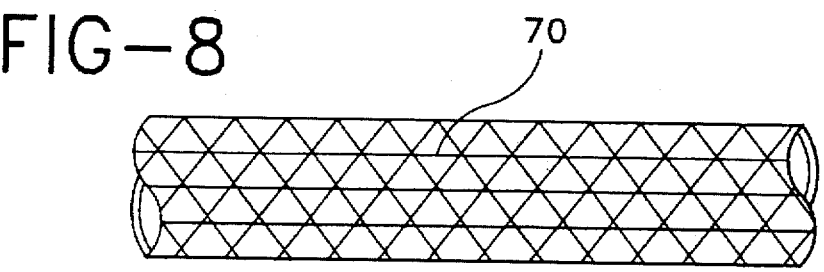
FIG. 8 is a side elevational view of an elongated braided structure having axial yarns therein.

After heat-setting, the braided structure would be able to stretch longitudinally until the axial yarns 70 become fully extended as illustrated in FIG. 8. The degree of stretch is controlled depending upon the geometry of the braid and the amount of compression during heat-setting.

Additionally, an axial yarn may be dyed and inserted into the braided structure subsequent to or during the braiding process. A dyed axial yarn positioned in the outer surface of the prosthesis aids the surgeon during implantation to indicate whether the prosthesis is straight and not twisted during the procedure. Preferably, the dyed axial yarn is black in color, formed from 70 denier, 54 filament type 55A Dacron™ polyester, produced by Dupont.

A three-dimensional, soft tissue prosthesis formed in accordance with the present invention may be formed by first choosing a mandrel with an outside diameter corresponding to an inside diameter of a natural body lumen which is to be replaced and thereafter braiding a three-dimensional braided structure onto the mandrel. The braided structure is preferably scoured at 80° C. in a water and detergent bath, and thoroughly rinsed, dried, and then rinsed in a hot water bath at about 70° C. to remove trace chemicals and dried. Subsequent to the scouring process, the braided structure is preferably heat-conditioned at a sufficient time and temperature to heat-set the synthetic material forming the prosthesis. Generally, heat-conditioning causes the graft to shrink slightly and densify. The heat-conditioning parameters are chosen based upon the properties of the synthetic yarns being used to form the braided structure. Typically, heat-conditioning is carried out at a temperature range from about 125° C. to about 225° C. using a convection oven for a time of about 20 minutes. Naturally, any known means for heating the structure may be used.

The soft tissue prosthesis and, more specifically a vascular graft formed in accordance with the preferred embodiment of the present invention preferably includes four layers made of thermoplastic yarns. The first layer or layers forming the intraluminal surface is preferably formed from a braiding element having a fine denier and braided to have a straight, smooth surface and small pores to prevent leakage of blood flowing through the vascular graft. A second layer in the multi-layered structure is preferably formed from a braiding element having stiffening properties. A third layer is preferably formed from a fusible component to further enhance the ravel resistance and fray resistance of the braided structure. A fourth or outer layer is preferably formed from a braiding element which provides the outer layer with a textured surface having relatively large pores to permit ingrowth of surrounding tissue into the vascular graft. Upon completion of the braiding process, the four layer braid formed in accordance with the present invention is preferably heat-conditioned to heat-set the thermoplastic yarns in position and to melt the fusible layer to be integrally formed into the braided structure.

The specifications of the yarns which may be used to form a soft tissue prosthesis in accordance with the embodiments of the present invention are set forth in the following examples. These examples are presented for purposes of illustration only and are not intended to limit the scope of the invention.

EXAMPLE 1

The first example refers to a 6 mm tubular prosthesis formed from an interlocked three-dimensional, multi-layered braided structure. The prosthesis is preferably braided on a mandrel at a braid angle of about 54.5°. The prosthesis includes four interlocked layers made from a variety of yarns. The first or inner (intraluminal) layer is formed from polyethylene terephthalate (PET) polyester yarns, 50 denier, flat, 48 filaments having 48 ends (ends refer to the number of carriers within the braiding machine). The second layer is formed having a fusible component. More specifically, this layer includes a 40 cotton count (spun) Cellbond™ fusible yarn having 12 ends and a 50 denier, flat, PET polyester yarn having 48 ends. Cellbond™ is a biocomponent yarn which has a core and sheath, whereby the sheath has a different melting temperature than the core. The third layer is formed from a 3 mil diameter PET monofilament yarn having 48 ends. This yarn provides the braided prosthesis with a stiffening component. The fourth (outer) layer is formed of PET polyester 50 diener, textured, 48 filament yarn with 48 ends. Upon completion, the braided structure is cleaned or scoured and subsequently heat-conditioned in a convection oven at about 175° C. for about 20 minutes to melt the fusible component and heat-set the PET polyester yarns.

EXAMPLE 2

The second example refers to a 6 mm tubular prosthesis formed from a three-dimensional, multi-layered interlocked braided structure having axial yarns. The structure is preferably braided on a mandrel and includes four layers. The axial yarns may be placed in all the layers or in a single layer. In this example, the axial yarns are placed in the third layer. The first or inner layer is formed from 50 denier, 48 filament, flat PET polyester having 48 ends. The second layer includes a fusible component formed from 40 cotton count Cellbond™ yarn having 12 ends and a 50 denier, flat PET polyester yarn having 36 ends. The third layer includes 24 ends of axial yarns formed from 50 denier, textured PET polyester and a stiffening component made from 3 mil diameter PET monofilament yarn having 48 ends. The fourth or outer layer is formed from a 50 denier, 48 filament, textured PET polyester yarn having 48 ends. Upon completion, the braided structure is cleaned or scoured and subsequently heat-conditioned in a convection oven at a temperature of about 175° C. for about 20 minutes to melt the fusible component and heat-set the PET polyester yarns.

EXAMPLE 3

The third example refers to a 6 mm tubular prosthesis formed from a solid three-dimensional braided structure having six strands forming three plys which are interbraided through the thickness of the braid. The prosthesis is formed from 50 denier, 48 filament, textured PET polyester yarn on each carrier in the machine, for a total of 144 ends (48 ends per pair or set of yarns). Upon completion of the braid, the structure is cleaned and subsequently heat-conditioned in a convection oven at temperature of about 175° C. for about 20 minutes to heat set the PET polyester yarns.

EXAMPLE 4

The fourth example refers to a 6 mm tubular prosthesis formed from a solid three-dimensional braided structure as described in Example 3, further including axial yarns. The braided structure includes 24 axial yarns of 70 denier, 54 filament, Type 55A Dacron textured PET polyester. The axial yarns are positioned in the center of the solid three-dimensional braid as illustrated in FIG. 5, reference numeral 52. Once again, this structure is preferably cleaned and subsequently heat-conditioned in a convection oven at a temperature of about 175° for about 20 minutes to heat-set the PET polyester yarns.

EXAMPLE 5

The fifth example refers to a 6 mm tubular prosthesis formed from a laminated or fused multi-layered three-dimensional structure. Each layer is formed from a two-dimensional braid which is bonded to its contiguous layer to form the three-dimensional braided structure. Thus, the first layer is braided over a mandrel, the second layer is braided over the first layer, the third layer is braided over the second layer and the fourth layer is braided over the third layer. Each layer is preferably braided having a braid angle of about 54.5°. The first or inner layer is formed from 50 denier, 48 filament, flat PET polyester having 48 ends. The second layer includes a fusible component and is formed from 24 ends of 40 cotton count Cellbond™ along with 24 ends of 50 denier, textured PET polyester. The third layer is braided having a stiffening component and a fusible component. The third layer includes 24 ends of 40 cotton count Cellbond™ along with 24 ends of 3 mil diameter, monofilament PET polyester. The fourth or outer layer is formed from 48 ends of 50 denier, 48 filament, textured PET polyester yarn. Thus, the fusible component is present on the inner layers (second and third layers) to bond the four braided layers together to form the three-dimensional structure. The three-dimensional structure is then cleaned and subsequently heat conditioned in a convection oven at a temperature of about 175° C. for about 20 minutes to melt the fusible component and heat set the PET polyester components.

A suitable apparatus for forming a solid three-dimensional braid in accordance with one embodiment of the present invention is disclosed in U.S. Pat. No. 4,719,837, entitled "Complex Shaped Braided Structures." According to the braiding process disclosed in the above-referenced patent, the braided structure is formed by moving the braiding yarns in a repeating two-step pattern such that the braiding yarns follow diagonal paths through a multi-layered axial array of yarns that extend longitudinally in the structure. Each of the braiding yarns pass completely through the array before reversing at a point outside of the array. The structure formed by this type of braiding machine is illustrated in FIGS. 3, 4 and 5.

A suitable apparatus for forming a tubular interlocking multi-layered three-dimensional braid in accordance with the preferred embodiment of the present invention is disclosed in the specification as published under International Patent Publication No. WO 91/10766. According to the braiding apparatus and method for forming the braid disclosed in the above-referenced publication, a braided structure is formed having a plurality of interlocked layers. The apparatus for producing such a braided object incudes: a two-dimensional array of rotatable horn gears in toothed engagement; a driving means for driving said array, each horn gear being arranged to rotate in a direction contrary to each interengaging gear; track means overlaying said array; and a plurality of yarn package carriers movable along said track means by said horn gears. The track means includes a plurality of track modules which together define a plurality of serpentine paths extending in a first direction and in which selected track modules include at least one cross-over path section extending in a second direction between one serpentine path and the next adjacent serpentine path to cause or allow the package carriers to move between adjacent serpentine paths to effect interbraiding of yarns between adjacent layers. The braided structure formed by this machine is illustrated in FIG. 1.

In order to form the laminated multi-layered braided structure, any known two-dimensional conventional braiding machine may be used. Each layer of the structure is braided on top of its contiguous layer to form the three-dimensional structure as illustrated in FIG. 6. As previously described, the layers of this structure are bonded together by any known technique.

Although the illustrative embodiments of the present invention have been described herein with reference to the accompanying drawings, it is to be understood that the invention is not limited to those precise embodiments, and that various other changes and modifications may be effected therein by one skilled in the art without departing from the scope or spirit of the invention.

What is claimed is:

1. An implantable tubular prosthesis, comprising:

a continuous elongate hollow three-dimensional braided structure having a plurality of layers in which at least one yarn of each layer extends into an adjacent layer to interlock said layers, said structure having an intraluminal fluid contacting surface and an outer tissue contacting surface along its length thereof; and wherein at least one of said layers includes a fusible component which upon melting integrally bonds said layers for enhanced resistance to ravelling and fraying.

2. The prosthesis according to claim 1, wherein said fusible component comprises a bicomponent yarn having a high melting temperature core and a low melting temperature polymer sheath.

3. The prosthesis according to claim 1, wherein at least one of said layers includes a stiffening component which is subsequently heat-set for increased radial stiffness of said structure.

4. The prosthesis according to claim 3, wherein said stiffening component comprises a monofilament yarn.

5. The prosthesis according to claim 1, wherein both said intraluminal surface and said outer surface include pores, and wherein said pores on said outer surface have on average pore size greater than said pores on said intraluminal surface, and wherein the average pore size changes progressively from said outer surface to said intraluminal surface.

6. The prosthesis according to claim 5, wherein said pores form a tortuous path from said intraluminal surface to said outer surface.

7. The prosthesis according to claim 6, wherein said braided structure has a porosity as determined by water permeability of less than about 100 ml/minute/cm$^2$.

8. The prosthesis according to claim 1, wherein said braided structure is impregnated with a leak resistant material.

9. The prosthesis according to claim 1, wherein at least one of said layers includes an axial yarn to control longitudinal extension thereof.

10. The prosthesis according to claim 1, wherein said braided structure is formed from yarns having a denier of from about 40 to about 300.

11. The prosthesis according to claim 10, wherein said intraluminal surface is formed from a fine denier yarn and said outer surface is formed from a heavy denier yarn.

12. The prosthesis according to claim 1, wherein said braided structure is formed with a braid angle of from about 54.5° to about 75°.

13. The prosthesis according to claim 1, wherein said braided structure is formed with a longitudinal stretch of from about 10% to about 25%.

14. The prosthesis according to claim 1, wherein said braided structure includes:

a first layer which forms said intraluminal surface and includes a fine denier yarn for providing said intraluminal surface with smooth low-porosity characteristics;

a second layer which forms said outer surface and includes a heavy denier yarn for providing said outer surface with textured high-porosity characteristics; and third and fourth layers positioned therebetween, one of said third and fourth layers including a monofilament component which is subsequently heat-set for imparting stiffening properties to said braided structure and the other of said third and fourth layers including a fusible component which upon melting integrally bonds said layers for enhanced resistance to ravelling and fraying.

15. An implantable tubular prosthesis, comprising:

a three-dimensional braided structure having a plurality of layers in which at least one yarn of each layer extends into an adjacent layer to interlock said layers, said structure having an intraluminal surface and an outer surface; and wherein both said intraluminal surface and said outer surface include pores, and wherein said pores on said outer surface have an average pore size greater than said pores on said intraluminal surface, and wherein the average pore size changes progressively from said outer surface to said intraluminal surface.

* * * * *